United States Patent
Guenther et al.

(10) Patent No.: US 6,461,715 B1
(45) Date of Patent: Oct. 8, 2002

(54) ARTICLE CLOSURE TAPE FOR AN ABSORBENT

(75) Inventors: Werner Guenther, Neuss (DE); Lloyd S. Eynon, Swansea (GB)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 09/462,979

(22) PCT Filed: Jul. 9, 1998

(86) PCT No.: PCT/US98/14228
§ 371 (c)(1),
(2), (4) Date: Jan. 14, 2000

(87) PCT Pub. No.: WO99/03437
PCT Pub. Date: Jan. 28, 1999

(30) Foreign Application Priority Data

Jul. 15, 1997 (EP) .............................. 97112042

(51) Int. Cl.[7] .................................. B32B 3/10
(52) U.S. Cl. ................ 428/131; 428/136; 428/198; 428/117.3; 428/149; 428/99; 428/343
(58) Field of Search ................. 428/131, 136, 428/198, 343, 117.3, 149, 99

(56) References Cited

U.S. PATENT DOCUMENTS

| | | |
|---|---|---|
| RE24,906 E | 12/1960 | Ulrich |
| 3,800,796 A | 4/1974 | Jacob |
| 4,036,233 A | 7/1977 | Kozak |
| 4,063,559 A | 12/1977 | Tritsch |
| 4,599,265 A | 7/1986 | Esmay |
| 4,643,729 A * | 2/1987 | Laplanche .......... 604/389 |
| 4,710,536 A | 12/1987 | Klingen et al. |
| 4,795,456 A | 1/1989 | Borgers et al. |
| 4,834,820 A | 5/1989 | Kondo et al. |
| 4,857,067 A | 8/1989 | Wood et al. |
| 5,344,691 A | 9/1994 | Hanschen et al. |
| 5,354,597 A | 10/1994 | Capik et al. |
| 5,501,679 A | 3/1996 | Krueger et al. |
| 5,885,908 A * | 3/1999 | Jaeger et al. .......... 442/59 |

FOREIGN PATENT DOCUMENTS

| | | |
|---|---|---|
| DE | 37 10037 A1 | 10/1998 |
| EP | 0 191 355 | 8/1986 |
| EP | 0 247 855 B1 | 5/1987 |
| EP | 0 249 073 B1 | 5/1987 |
| EP | 0 529 681 A1 | 12/1988 |
| EP | 0 487 758 B1 | 11/1990 |
| EP | 0 704 196 A1 | 9/1994 |
| EP | 0 736 585 A1 | 4/1995 |
| WO | WO 81/03601 | 12/1981 |
| WO | WO 93/13148 | 7/1993 |
| WO | WO 96/10382 | 4/1996 |

* cited by examiner

Primary Examiner—Blaine Copenheaver
Assistant Examiner—Hai Vo
(74) Attorney, Agent, or Firm—Gary L. Griswold; Robert W. Sprague; William J. Bond (57) ABSTRACT

The present invention refers to a closure tape (10) for an absorbent article, particularly for a disposable diaper (1), for fastening of the article on the body of a person, the closure tape being attachable to the outside surface (3) of the diaper (1) through one of its end portions (17) and comprising a backing (11) bearing a continuous or discontinuous adhesive layer (12), a fastening means (15) and a stretchable elastic sheet (13), the backing (11) being essentially non-elastic and/or essentially non-extensible, the support sheet comprising the backing (11) and the continuous or discontinuous adhesive layer exhibiting one or more incisions (14) in the area of the elastic sheet with at least one of the incisions extending in machine direction over the full width of the backing (11) and the end portion (17) being separated from the incision (14) closest to the end portion (7), by a sufficiently large distance (22) to prevent the incisions (14) essentially from opening when attaching the end portion (17) to the outside surface (3) of the diaper (1) and bending the remaining part of the closure tape (10) to contact the inside surface (2) of the diaper (1).

10 Claims, 6 Drawing Sheets

ARTICLE CLOSURE TAPE FOR AN ABSORBENT

FIELD OF THE INVENTION

The invention relates to a closure tape for an absorbent article, particularly for a disposable diaper, for fastening of the article on the body of a person, said closure tape being attachable to the absorbent article through one of its end portions and comprising a backing, a fastening means and an elastic sheet to render the closure tape elastically stretchable. The invention furthermore relates to a prelaminated closure tape in a stable roll from which the closure tape can be cut.

BACKGROUND OF THE INVENTION

Absorbent articles such as disposable diapers are provided with closure tapes which are anchored to the absorbent article through one of its end portions by means of, for example, a pressure-sensitive adhesive layer. The opposite end portion of the closure tape comprises a fastening means to close the absorbent article around the wearer's body and fasten the absorbent article on the body. Among these closure tapes, there have also been described elastically stretchable tapes to improve the fit and the comfort of the absorbent article.

U.S. Pat. No. 3,800,796 discloses a diaper with semi-elastic strip fasteners having a freely extensible elastic central segment and two non-extensible inelastic terminal segments. A similar construction is also described in EP 0,249,073 wherein the boundary regions between the elastic middle portion and the two non-elastic end portions are formed by melt-extrusion of both or either of the elastic material and the non-elastic material in order to provide integral bonding between the segments. EP 0,247,855 provides a composite prelaminated closure tape which can be dispensed from a stable roll form to provide a closure with a central elastomeric sheet. The prelaminated closure tape is securely fastened to the inside and outside surface of one edge of the diaper. The attached closure tape comprises a central elastomeric portion and two anchor strips as end portions.

The elastically stretchable closure tapes described in U.S. Pat. No. 3,800,796, EP 0,249,073 and EP 0,247,855 comprise an elastic middle portion between two non-elastic end portions or anchor strips. While these closure tapes are useful and of commercial importance they are sometimes disadvantageous in that the method of preparing them is relatively complicated and requires secure bonding of the tape segments.

In another group of references the elastically stretchable closure tape comprises an elastic backing. U.S. Pat. No. 4,063,559 discloses a disposable diaper with a closure tape having an extendible or stretchable backing made from a variety of materials comprising, for example, plasticized polyvinyl chloride films, polyolefin films, polyurethane films, vinyl chloride and vinylidene chloride copolymer films, rubber hydrochloride films, polyamide films or elastomeric films derived from styrene-butadiene or styrene-isoprene block copolymers. The backing bears an adhesive layer with a partible protective cover means on top of it. The protective cover is substantially coextensive with the adhesive coating when the closure tape is in a non-extended storage position, but is parted when the closure tape is stretched into the working position, thereby making portions of the adhesive coating available for use in securing the diaper to the body of an infant. The protective cover means may comprise discontinuous slits which form discrete apertures when stretched. Alternatively, the protective cover means may be an embossed, rupturable thermoplastic web or a unitary web provided with spaced, weakened regions which rupture when the web is stretched.

EP 0,191,355 discloses a fastening tape for a disposable diaper comprising a base tape or a backing carrying thereon an adhesive layer wherein the backing when subjected to stress (tension) and subsequently strain (elongation), shows a hysteresis curve with a hysteresis loss ratio of between 20 to 80%. The backing may include a plurality of weakened areas in various geometrical shapes (see FIGS. 9–12), among them discontinuous slits extending orthogonally with respect to the long axis of the backing (cross direction). In an alternative embodiment, EP 0,191,355 describes a fastening tape having two non-elastic end portions and an elastic middle portion made from an elastic material having a hysteresis loss ratio of between 20 to 80%. Using closure tapes with elastically stretchable backings is sometimes disadvantageous because the closure tape which is attached to the diaper may exhibit an insufficient rigidity orthogonal to the long axis of the backing (machine direction) and be floppy.

EP 0,704,196 describes a fastening tape having a stretchable elastic portion which is a sandwich structure of a stretchable elastic tape and a non-elastic backing whereby the elastic tape is secured to the non-elastic backing at least at both ends thereof to bridge a section of the backing which is longer than the elastic tape section and may assume, for example, a zigzag folding shape. If the fastening tape is stretched into a predetermined position, the elastic tape extends and the zigzag-form of the non-elastic backing disappears. The rigidity of the fastening tape in machine direction in the relaxed state is determined by the non-elastic backing. In the construction of EP 0,704,196 it is sometimes difficult to reliably adhere the elastic tape to the zigzag-shaped non-elastic backing.

U.S. Pat. No. 4,834,820 discloses a closure tape having an elastic sheet extending over the whole length of the closure tape and a non-flexible retaining sheet partly bonded to the flexible sheet. The retaining sheet may comprise one or two cut-off grooves. The retaining sheet is ripped apart along the cut-off grooves thus rendering the closure tape elastic, and the central portion of the retaining sheet may be removed in one embodiment (FIGS. 4 and 5). The closure tape is claimed not to interfere with the abdominal respiration of the baby after wearing and eliminates the need for peeling off the tape for checking for urination and stool.

U.S. Pat. No. 4,795,456 discloses an extensible diaper closure tape which comprises an extensible layer 4 uninterruptedly extending over the whole length of the tape. The extensible layer bears on one side a carrier web layer with an unwind release coating the carrier web layer being attached to the flexible layer with a first adhesive layer. The carrier web layer exhibits one or more incisions, and the adhesive layer beneath the slits may or may be not be removed. The other side of the extensible layer carries a second adhesive layer which may be slitted in the same area where the first adhesive layer on the opposite side of the extensible layer exhibits an incision. A non-extensible layer bearing on the exposed side a third adhesive layer, is attached to the second adhesive layer. The non-extensible layer is permanently adhered to the second adhesive layer in the area from the manufacturer's end to the incisions, and it is releasably adhered to the second adhesive layer in the area from the user's end to the incisions. The tape is attached to the outside surface of the diaper with the third adhesive layer at the manufacturer's end and bent around the edge portion of the diaper thus adhering the user's end with the third adhesive layer to the inside surface of the diaper prior to use. When deployed, the closure tape opens along the release coating between the second adhesive layer and the non-extensible layer which remains adhered to the edge portion of the diaper. The user's end which has been rendered flexible by the deployment can be used to secure the diaper to the wearer. The closure tape of U.S. Pat. No. 4,795,456 is non-extensible in the initial state prior to use but rendered extensible on deployment which is advantageous. On the other hand, the closure tape is secured to the outside surface of the diaper only. This peel mode type of attachment offers a relatively low bonding strength and may fail when securing the diaper around the wearer's body or during use. Prior to deployment, the slits which are in the area where the tape is being bent around the edge portion of the diaper, open at least partly thus rendering the surface of the tape coarse which is less preferred. The slits are furthermore easily contaminated.

Therefore there was a need for an elastically stretchable closure tape which is easy to manufacture and does not exhibit the shortcomings of the closure tapes available in the state of the art or exhibits them to a lower degree only. Other objects of the present invention are evident from the following detailed description of the invention.

SUMMARY OF THE INVENTION

The present invention refers to a closure tape 10 for an absorbent article, particularly for a disposable diaper 1, for fastening of the article on the body of a person, the closure tape 10 being attachable to the outside surface 3 of the diaper 1 through one of its end portions 17 and comprising a backing 11 bearing a continuous or discontinuous adhesive layer 12, a fastening means 15 and a stretchable elastic sheet 13, the backing 11 being essentially non-elastic and/or non-extensible, the support sheet 20 comprising the backing 11 and the continuous or discontinuous adhesive layer 12 exhibiting one or more incisions 14 in the area of the elastic sheet with at least one of the incisions extending in the machine direction (direction orthogonal to the long axis of the closure tape) over the full width of the backing 11, and the end portion 17 being separated from the incision 14 closest to 10 the end portion 17, by a sufficiently large distance 22 to prevent the incisions 14 essentially from opening when attaching the end portion 17 to the outside surface 3 of the diaper 1 and bending the remaining part of the closure tape 10 to contact the inside surface 2 of the diaper 1.

The invention furthermore refers to a prelaminated closure tape in a stable roll from which the closure tape 10 according to the invention can be cut, and to an absorbent article, in particular a diaper 1, comprising a closure tape according to the invention.

DETAILED DESCRIPTION OF THE INVENTION

The closure tapes 10 of the present invention are useful and beneficial when attached to an absorbent article and, in particular, to a disposable absorbent article. As used herein, the term "disposable absorbent article" refers to articles which are placed against or in proximity to the body of the wearer to absorb and contain the various exudates discharged from the body and which are intended to be disposed of after single use (i.e., they are not intended to be laundered or otherwise restored or reused).

A preferred embodiment of the disposable absorbent article of the present invention is a diaper. As used herein, the term "diaper" refers to a garment generally worn by infants or incontinent persons that is drawn up between the legs and fastened about the waist of the wearer.

Figure 1:
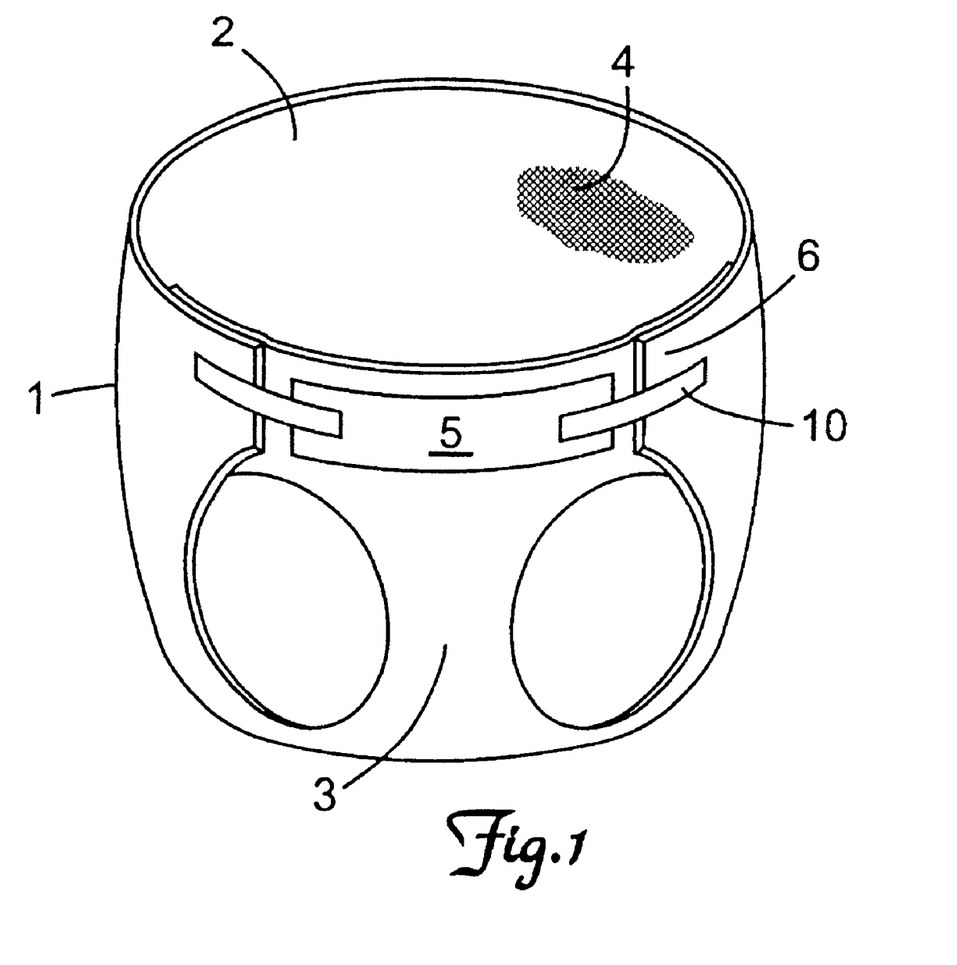
FIG. 1 is a perspective representation of a disposable diaper 1 in a closed form, said diaper having an absorbent core 4 between an inside surface 2 and an outside surface 3, closure tapes 10 anchored to the edge portions 6 of the diaper and fastened to the target area 5 on the outside surface of the diaper.

FIG. 1 is a partially cut-away perspective representation of a disposable diaper 1 in a closed form. The diaper comprises an absorbent core 4 between an inside surface 2 and an outside surface 3. The absorbent core 4 may be any means which is generally compressible, conformable, non-irritating to the wearer's skin, and capable of absorbing and retaining liquids and certain body exudates.

The outside surface 3 of the diaper is impervious to liquids and is preferably manufactured from a thin plastic film, although other flexible liquid impervious materials may also be used. The outside surface 3 prevents the exudates absorbed and contained in the absorbent core 4 from soiling articles which contact the diaper 1 such as bedsheets and undergarments.

The inside surface 2 of the diaper is compliant, soft-feeling, and non-irritating to the wearer's skin. Further, the inside surface 2 is liquid previous permitting liquids to readily penetrate through its thickness. A suitable inside surface 2 may be manufactured from a wide range of materials such as porous foams, reticulated foams, apertured films, natural fibers (e.g., wood or cotton fibers), synthetic fibers (e.g., polyester or polypropylene fibers) or from a combination of natural and synthetic fibers. Preferably, it is made of a hydrophobic material to isolate the wearer's skin from liquids retained in the absorbent core 4. A suitable inside surface 2 may be, for example, a spunbond or carded polypropylene nonwoven of approximately 15–25 g/m$^2$.

The absorbent core 4 may be secured to the outside surface 3 by means of, for example, pressure-sensitive adhesives, hot melt adhesives or other adhesives, ultrasonic bonding or heat/pressure sealing. The outside surface 3 and the inside surface 2 may be joined to each other directly or indirectly by using an intermediate fixing member to which the outside surface 3 and the inside surface are affixed. The inside surface 2 and the outside surface 3 may be associated together by various means comprising, for example, pressure-sensitive adhesives, hot melt adhesives or other adhesives, ultrasonic bonding and/or heat/pressure.

The above description of the diaper 1 is meant to be explanatory only and not limiting. Further details on diapers and their construction are described in literature and may be taken, for example, from EP 0,529,681, U.S. Pat. No. 4,036,233, EP 0,487,758, WO 96/10,382, U.S. Pat. No. 3,800,796, EP 0,247,855 or U.S. Pat. No. 4,857,067.

Figure 5:
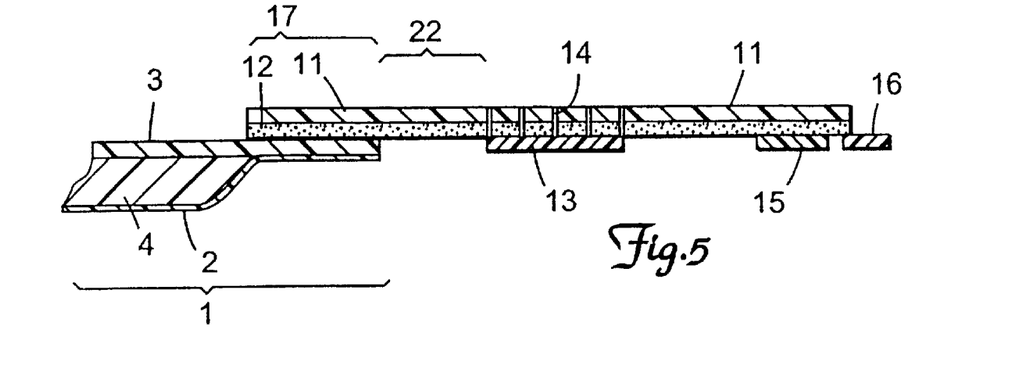
FIG. 5 is a schematic cross-sectional view of the embodiment of the closure tape 10 of FIG. 2 (relaxed state) being attached to the outside surface 3 of the diaper only in a peel mode type of attachment.
Figure 6:
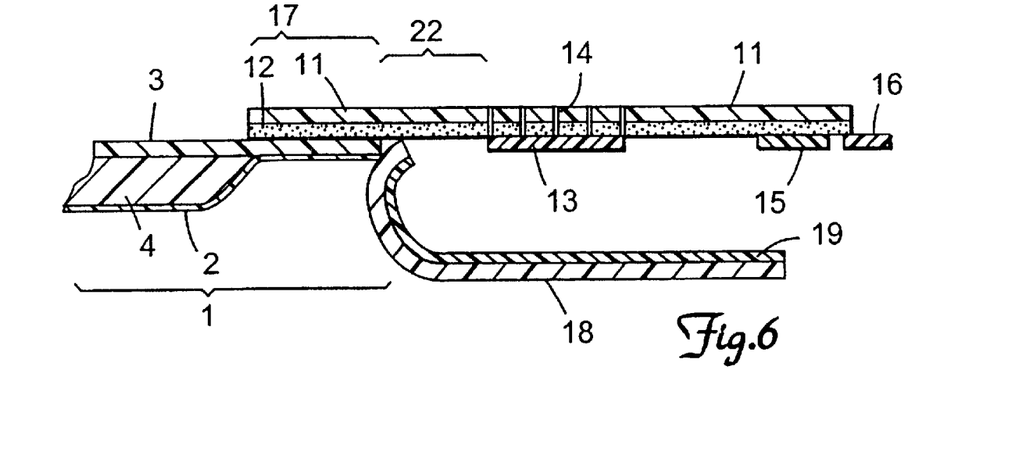
FIG. 6 is a schematic cross-sectional view of the embodiment of the closure tape of FIG. 2 (relaxed state) which is attached to the outside surface 3 of the diaper 1 and which is additionally attachable to the inside surface 2 of the diaper 1 by means of release sheeting 19 bearing adhesive layer 18 to provide for a shear mode type or Y type of attachment.

The closure tape 10 is secured to the edge portion 6 of the diaper 1. The closure tape 10 can be attached only to the outside surface 3 of the diaper as shown in FIG. 5 or both to the outside surface 3 and inside surface 2 of the diaper as can be taken from FIG. 6 in order to anchor the closure tape 10 to the diaper 1. The anchoring mode shown in FIG. 5 is termed as peel mode type attachment offering a relatively low bonding strength. Peel mode type anchored closure tapes 10 may loosen when attaching the diaper to the wearer's body and during use so that this type of attachment is usually less preferred. The closure tape 10 shown in FIG. 6 is additionally attachable to the inside surface 2 of the diaper by means of release sheeting 19 bearing adhesive layer 18 to provide a shear mode or Y mode type of attachment. This type of anchoring reliably secures the closure tape 10 to the diaper and is preferred.

Alternatively the manufacturer's end can be bonded in between the outside surface 3 and the inside surface 2 of the diaper.

In the closed state of the diaper 1, the fastening means 15 of the closure tape 10 is attached to the target area 5. The target area 5 may be formed of an additional strip which is attached to the outside surface 3 of the diaper 1 in such a manner that the size of the diaper or garment may be adjusted in accordance with the size of the user. The target area can comprise one or more such strips and could also form the entire outside surface 3 of the diaper. The outer surface of the target area 5 is selected to engage with the fastening means 15 of the closure tape 10 in an overlapping configuration to provide a secure side closure. For example, in case the fastening means 15 is a mechanical fastening means and comprises a hook material, the outer surface of the target area will comprise any suitable material which interlocks with hook material such as, for example, woven or non-woven fabrics.

Figure 2:
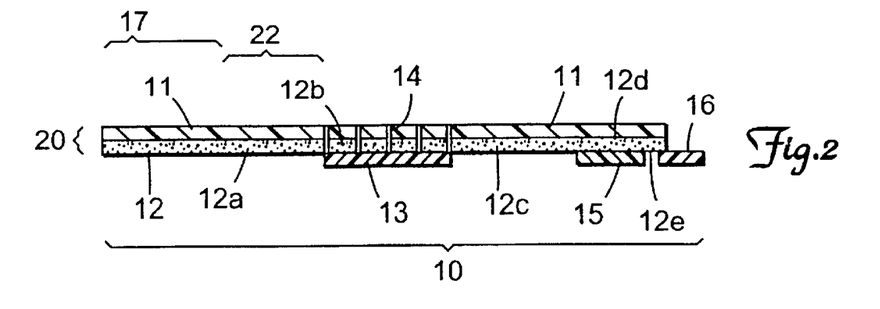
FIG. 2 is a cross-sectional view of a preferred embodiment of the closure tape 10 in the relaxed state (no tension forces applied), said closure tape having a support sheet 20 comprising a backing 11 bearing a continuous adhesive layer 12 in areas 12a–12e, an elastic sheet 13, fastening means 15, a finger-lift 16 and incisions 14 in the area 12b of the elastic sheet 13. The manufacturer's end 17 is separated from the incision 14 closest to it, by the distance 22, and the user's end 21 comprises the fastening means 15, the adhesive area 12e and the finger-lift 16.

The absorbent article and, in particular, the disposable diaper 1 of the present invention differs from prior art contoured absorbent articles in that it comprises a novel closure tape 10. Reference is made to FIG. 2 which shows a cross-sectional view of a preferred embodiment of the closure tape.

The closure tape 10 of FIG. 2 comprises a backing 11 which is preferably selected from a group of materials which is essentially non-elastic and imparts a desirable stiffness to the closure tape 10.

For the purposes of the present invention a material is considered to be elastic in a given direction if a sample of the material (dimensions 25 mm×18 mm×0.1 mm) is stretchable in that direction from a first and generally relaxed length (no external tensional forces applied) to a second or expanded length which is at least two times the first length and upon relaxation, will retract to a third length which is no greater than 1.1 times the first length with these figures referring to the second tension-relaxation cycle. Materials which irreversibly deform when a sample of the material (dimension 25 mm×18 mm×0.1 mm) is stretched in a given direction from a first and generally relaxed virgin state (no external tension force, no cycle comprising application of tension force and release of tension force applied yet) to a second or expanded state with a length of 1.5 times the first length so that upon release of the tension force the material remains in the expanded state or retracts to a third state that is at least 1.25 of the first length, or which breaks before being stretched to a length of 1.5 times the original length, are termed as non-elastic with respect to the given direction.

Likewise, for the purposes of the present invention, a closure tape 10 having an elastic sheet 13 comprising a material which meets the above definition, is considered to be elastic or elastically stretchable.

For the purposes of the present invention a material is considered to be inextensible in a given direction if a force of at least 60 N has to be applied to stretch a sample of the material (length 100 mm, width 25 mm, thichness 0.1 mm) in that direction irreversibly or reversibly from a first and generally relaxed virgin state (no external tension force, no cycle comprising application of tensional force and release of tension force applied yet) to a second or expanded state with a length of 1.1 times the first length.

The backing 11 is preferably selected from a group of materials comprising polypropylene, polyvinylchloride, polyethylene terephthalate, polyethylene, polyolefin copolymers or blends of polyolefins such as, for example, blend of polypropylene and LPDE (low density polyethylene), nonwoven and foamed materials. The thickness of the backing is preferably between 50 $\mu$m and 500 $\mu$m, and more preferably between 100 $\mu$m and 400 $\mu$m.

Figure 8:
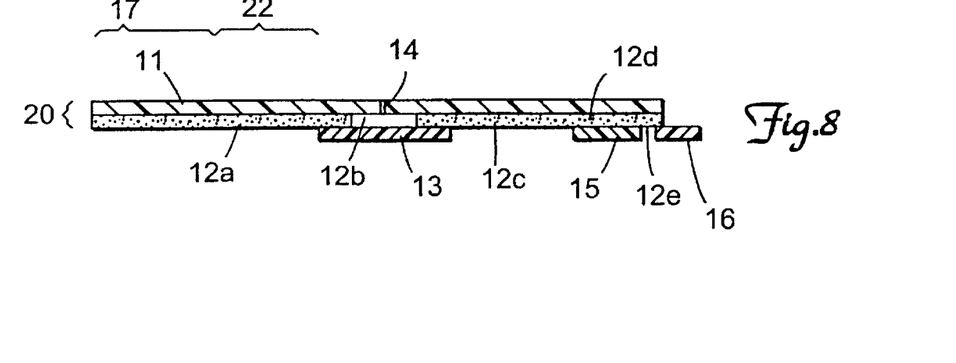
FIG. 8 is a cross-sectional view of another preferred embodiment of the closure tape 10 in the relaxed state, said closure tape 10 having a support sheet 20 comprising a backing 11 bearing a discontinuous adhesive layer in areas 12a, 12c, 12d and 12e, an elastic sheet 13, a fastening means 15, a finger-lift 16 and one incision 14 in the area 12b of the elastic sheet 13.

The backing 11 bears an adhesive layer 12 which may extend over the whole length of the closure tape 10 as is shown, for example, in FIG. 2 or which may cover only part of the backing as is shown, for example, in FIG. 8. The adhesive layer 12 may be conceptually divided into different areas 12a–12e whereby area 12a comprises the end portion 17 of the closure tape 10 and the distance 22 between the end portion 17 and the incision 14 closest to it. Area 12b is the part of the adhesive layer 12 in the area of the elastic sheet 13, area 12c corresponds to the area between the elastic sheet 13 and the fastening means 15, area 12d is the part of the adhesive layer 12 in the area of the fastening means 15 and area 12e is the part of the adhesive layer at the end of the closure tape bearing the finger-lift 16.

Figure 7:
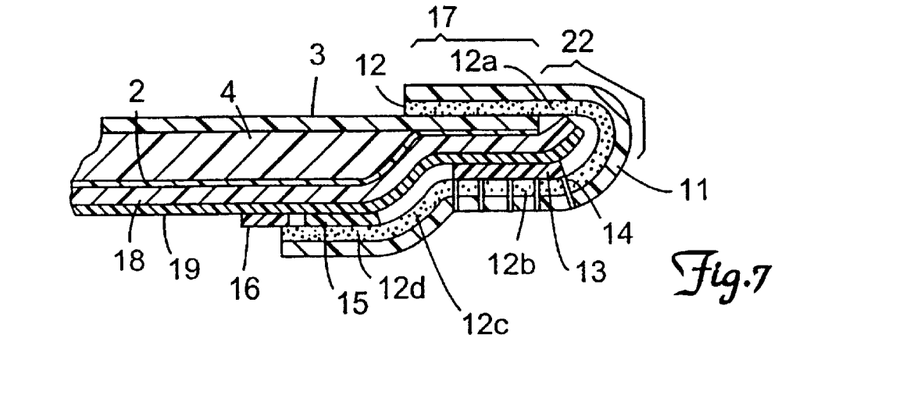
FIG. 7 is a schematic cross-sectional view of the embodiment of the closure tape of FIG. 2 before deployment with the closure tape 10 being folded over to contact the inside surface 2 of the diaper 1.

Part of the area 12a of the adhesive layer is used to anchor the end portion 17 of the closure tape 10 to the outside surface 3 of the disposable diaper as is shown, for example, in FIG. 6. The end portion 17 is also termed as manufacturer's end because it is used to attach the closure tape to the diaper 1 during its manufacture. The opposite end portion 21 of the closure tape 10 comprising fastening means 15, adhesive area 12e and finger-lift 16 is also termed as user's end because it forms the joint made by the user in securing the diaper to the wearer. The remaining part of the area 12a extends over the distance 22 between the manufacturer's end 17 and the incision 14 being closest to it. The adhesive layer 18 attached to the release sheeting 19 may be applied to this part of the adhesive layer 12a as is shown in FIG. 6. The distance 22 is selected to be sufficiently large to prevent the incisions 14 essentially from opening when attaching the manufacturer's end 17 to the outside surface 3 of the diaper 1 and bending the remaining part of the closure tape 10 to contact the inside surface 2 of the diaper 1 as is shown in FIG. 7. The distance 22 ensures that the incisions 14 remain essentially closed when storing the diaper in the state of FIG. 7 prior to use and prevent the incisions from getting contaminated. Furthermore, the surface of the backing offers an aesthetically pleasant and soft appearance.

The extension of distance 22 depends on the concrete construction of the diaper 1 and the closure tape, and it is preferably at least 2 mm, more preferably at least 3 mm and especially preferably at least 4 mm.

The adhesive used in area 12a of the adhesive layer is selected to permanently attach the manufacturer's end 17 to the outside surface 3 of the diaper 1 during its manufacture so that the closure tape is not removed from the outside surface 3 of the diaper when the diaper 1 is used and opened or closed several times. The adhesive useful for area 12a comprises pressure-sensitive adhesives including pressure-sensitive hot-melt adhesives and non-pressure-sensitive adhesives. The pressure-sensitive adhesives which are preferred, are preferably selected to exhibit a 90° peel adhesion from a polyethylene surface as measured according to a slightly modified test method FTM2, FINAT test method no. 2, FINAT Technisches Handbuch, 4. Auflage (1995), pp. 6–7 of at least 3.5 N/cm, more preferably of at least 5 N/cm and especially preferably of at least 6 N/cm. The test method used deviates from FTM2 in that a 150 $\mu$m polyethylene film STA-211 (thickness 150 $\mu$m ,adhered to a stainless steel substrate with a double-sided adhesive film) is used as the test substrate and in that the peel adhesion measurement is performed 2 min after applying the adhesive strip to the substrate. The pressure-sensitive adhesive furthermore preferably exhibits a high value of static shear as measured according to a slightly modified test method FTM8, FINAT test method no. 8, FINAT Technisches Handbuch, 4. Auflage (1995), pp. 15–16 of at least 100 min, more preferably of at least 300 min and especially preferably of at least 500 min to ensure that the diaper does not inadvertently come loose from the wearer's body. The test method used deviates from FTM8 in that a weight of 500 g is used instead of 1000 g, and that the temperature is 38±2° C. instead of 23±2° C. and that the test specimen comprises a synthetic rubber film as described in Example 1 as the test substrate and a propylene backing with a thickness of 110 $\mu$m with the adhesive to be tested attached to it as the adhesive strip which bears the weight.

Suitable pressure-sensitive adhesives include rubber-based adhesives (also called rubber-resin adhesives) which comprise natural or synthetic rubber materials and typically also tackifying resins in order to render the rubber materials tacky. Preferred examples of rubber-based pressure-sensitive adhesives are the polystyrene polyisoprene block copolymers tackified with synthetic polyterpene resins. Suitable pressure-sensitive adhesives furthermore include acrylate-based pressure-sensitive adhesives such as, for example, those disclosed in U.S. Pat. No. Re 24,906 or U.S. Pat. No. 4,710,536. The adhesives mentioned above are given only by way of example, and the person skilled in the art can select other adhesives known in the state of the art without any inventive effort. The thickness of the adhesive layer in the adhesive area 12a preferably is between 10 and 200 $\mu$m and more preferably between 20 and 100 $\mu$m.

The area 12b which corresponds to the area of the elastic sheet 13 may comprise an adhesive layer as is shown, for example, in FIG. 2 or may be essentially free of adhesive as is shown, for example, in FIG. 8.

In the embodiment of FIG. 2 the adhesive used in area 12b preferably is selected to reliably and permanently secure the elastic sheet 13 to the backing 11. The adhesive of area 12b may be pressure-sensitive or non-pressure-sensitive. Pressure-sensitive adhesives are preferred and in an especially preferred embodiment the adhesive of area 12b is the same adhesive as used in area 12a. The thickness of the adhesive layer in area 12b preferably is between 100 $\mu$m and 200 $\mu$m and more preferably between 20 and 100 $\mu$m. It is specifically preferred that the adhesive layer in area 12b has the same thickness as the adhesive layer in area 12a.

In case the area 12b is essentially free from adhesive the elastic sheet 13 may be bonded to the backing 11 in that the adhesive layers of areas 12a and 12c, respectively, are slightly extended into the area 12b with the extending adhesive sections supporting and adhering the elastic sheet 13 to the backing 11 as is schematically shown in FIG. 8. Alternatively or additionally, the elastic sheet 13 may also be attached to the backing 11 by different methods of welding such as heat welding or ultrasonic welding, respectively. Rotary ultrasonic welding is particularly preferred. Rotary ultrasonic welding devices are commercially available, for example, from Cera, Villars, France, and contact-free ultrasonic welding systems are commercially available from Hermann, Karisbad, Germany. Ultrasonic welding systems are also commercially available from Branson Company, U.S.A. In a specifically preferred embodiment the elastic sheet 13 is attached to the backing by using an adhesive layer extending fully or partly over area 12b additionally securing the ends of the elastic sheet by heat welding or ultrasonic welding and, in particular, by ultrasonic welding.

The area 12c between the elastic sheet 13 and the fastening means 15 may comprise an adhesive layer as is shown, for example, in FIG. 2 or may be essentially free of any adhesive. Using an adhesive in area 12c is especially advantageous in case the fastening means 15 comprises mechanical fastening means such as, for example, hook fastening means which may also be referred to as a male fastening means. Such hook fastening means require corresponding female fastening means such as, for example, fibrous elements of a loop fastening material on the target area to engage with in order to reliably secure the diaper around the wearer. Since the female fastening means is often essentially restricted to the target area 5, it will typically be tucked underneath other portions of the diaper on folding or rolling up the diaper for disposal. An exposed adhesive layer in area 12c can overcome this problem and offer an additional fastening means allowing for convenient disposal of the diaper.

An exposed or partially exposed adhesive layer in area 12c and/or area 12e releasably adheres the closure tape 10 when being bent over to attach the inside surface 2 of the diaper when storing the diaper prior to use (see FIG. 7) to the release sheeting 19. This prevents the closure tape in the bent-over state from "pop-open" which is desirable. Pop-open may also be prevented, for example, by releasable adhering the closure tape 10 to the inside surface 2 of the diaper or the release sheeting 19 by ultrasonic spot welding or spot heat bonding.

The adhesive optionally used in area 12c may be a pressure-sensitive adhesive or a non-pressure-sensitive adhesive. Preferably it is a pressure-sensitive adhesive, and the same adhesive as used in area 12a is preferably used. Optionally when using the adhesive of area 12a in area 12c, this adhesive may be partially deactivated, for example, by corona treatment in order to render the adhesive layer in area 12c less aggressive and removable. Alternatively, it is possible to cover area 12c prior to using it with a release liner which will be removed prior to fastening the rolled-up diaper 1 for disposal. It is furthermore possible to use a different pressuresensitive adhesive in area 12c which is less aggressive than the adhesive of area 12a and which allows the closure tape 10 to be removably attached to the outside surface 3 of the diaper. Suitable non-permanent acrylate-based pressure-sensitive adhesives are described, for example, in EP 0,736,585, WO 93/13,148 or U.S. Pat. No. 4,599,265. The thickness of the adhesive layer in area 12c preferably is between 10 $\mu$m and 200 $\mu$m and more preferably between 20 $\mu$m and 100 $\mu$m. The thickness of the adhesive layer in area 12c, if present, is especially preferably selected to be the same as the thickness of the adhesive layer in areas 12a and, if present, 12b.

The area 12d which corresponds to the area of the fastening means 15 comprises an adhesive layer which can be pressure-sensitive or non-pressure-sensitive. The fastening means 15 can be a mechanical fastening means, such as, for example, a hook material, or another adhesive layer which may be attached to a carrier sheet or directly laminated to the adhesive layer in area 12d. It is also possible that no additional fastening means 15 is attached to the adhesive layer in area 12d and that the adhesive layer in area 12d is used as fastening means 15.

In case an additional fastening means 15 is used, this being preferred, the adhesive used in area 12d preferably is an aggressive pressure-sensitive adhesive material in order to reliably secure the fastening means 15 to the backing 11. The pressure-sensitive adhesive may be selected from the group of adhesives described above for use in area 12a, and the same adhesive is preferably used in areas 12a and 12d. In case the additional fastening means 15 is omitted, the adhesive used in area 12d is selected so that the diaper can be both reliably secured to the wearer's body when being used, and be easily removed after use. The adhesion behavior of the adhesive used in area 12d with respect to the target area 5 is governed both by the nature of the adhesive and the surface properties of the target area 5. In case the adhesive layer of area 12d is used to fasten the diaper to the wearer's body, the target area 5 typically comprises a film which may have a release coating such as, for example, a BOPP film which is commercially available from 3M Company, St. Paul, U.S.A., as Frontal Tape KR-0827 or a cast polypropylene film which is commercially available from 3M Company, St. Paul, U.S.A. as Cast PP Frontal Tape KR-0822. When using an appropriate release surface in target area 5 it is often possible to use aggressive pressure-sensitive adhesives such as those described above for use in area 12a also for the adhesive layer of area 12d in case no additional fastening element 15 is present. Alternatively, the pressure-sensitive adhesive of area 12d may be partially detackified to render it less aggressive and removable from the target area 5.

The area 12e which corresponds to the area between the fastening means 15 and the end of the closure tape 10 carrying the finger-lift 16, usually is at least partly covered with an adhesive layer to reliably secure the finger-lift 16 to the backing 11. In the embodiment of FIG. 2 the area 12e is completely covered with an adhesive layer. The adhesive of area 12e may be a pressure-sensitive adhesive or a non-pressure-sensitive adhesive with a pressure-sensitive adhesive being preferred. Especially preferred are the pressure-sensitive adhesives described above for use in area 12a. Alternatively the backing 11 in area 12e may provide a finger-lift feature if the adhesive in area 12e is omitted; in this case no additional finger-lift is required.

The closure tape 10 preferably has a width or extension in cross direction of between 40 and 100 mm and more preferably of between 50 and 80 mm, and an extension in machine direction of preferably between 15 and 50 and more preferably of between 15 and 30 mm. These dimensions are given only by way of example and other dimensions can be used as well. The ratio of the extension in machine direction over the extension in cross direction is preferably between 0.15 and 0.50 and more preferably between 0.25 and 0.40.

The extensions of areas 12a–12e are highly variable and may be optimized in view of a specific design of a closure tape 10 according to the present invention. Area 12a corresponding to the manufacturer's end 17 typically has an extension in cross direction of between 10 and 30 mm and more preferably of between 12 and 25 mm. The dimensions of areas 12b and 12d, respectively, preferably essentially correspond to the dimensions of the elastic sheet 13 and the fastening means 15, respectively, which are given below. The fastening means 15 can be located directly adjacent to the elastic sheet 13 so that area 12c can be omitted. Area 12c preferably has an extension in cross direction of between 0 and 20 mm and, more preferably, of between 0 and 15 mm. The extension of area 12e may in cross direction preferably is between 0 and 10 and more preferably between 0 and 8 mm. Area 12e may be omitted, for example, in case no finger-lift 16 is used or in case a mechanical fastening means 15 is used which simultaneously can provide a finger-lift feature.

The adhesive layer 12 may be present in some or all of the areas 12a–12e and/or may be present in additional areas corresponding to further optional features of the closure tape such as, for example, a release liner to cover the adhesive layer of area 12c.

The adhesive layer 12 can be applied to the backing 11 using different techniques such as, for example, solvent coating, hot-melt coating, spray coating, slot coating, swirl coating and lamination. Discontinuous adhesive layers can be obtained using different techniques such as, for example, strip coating, lamination or screen printing.

The closure tape 10 comprises an elastic sheet which in combination with one or more incisions (also termed as slits) 14 vertically extending from the surface of the backing 11 through the area 12b to the upper surface of the elastic sheet 13, render the closure tape 10 elastically stretchable in cross direction (CD) thus increasing the fit and the comfort of the absorbent article. In case of mechanical fastening means 15, the elastic sheet 13 exerts a restoring force onto the joint formed between fastening means 15 and target area 5 which is advantageous in order to reliably secure, for example, the diaper 1 around the wearer's waist. The cross direction which is shown in FIG. 3 corresponds to the longitudinal symmetry axis of the closure tape 10 and is orthogonal to the machine direction (MD, also shown in FIG. 3) or lateral symmetry axis.

Figure 3:
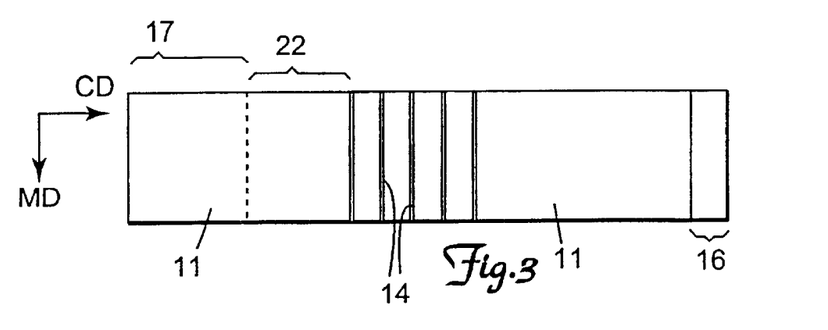
FIG. 3 is a top view of the embodiment of the closure tape 10 of FIG. 2 in the relaxed state, showing the backing 11 bearing parallel incisions 14 in the area 12b of the elastic sheet 13 which extend over the full width of the closure tape 10 in the machine direction.

The elastic sheet 13 preferably extends in the machine direction over the full width of the closure tape as is shown in FIG. 3. It is, however, also possible that the elastic sheet 13 extends only partly over the full width of the closure tape in machine direction and exhibits, for example, a triangular shape. It is also possible, though less preferred, that the extension of the elastic sheet 13 in machine direction is less than the full width of the closure tape over the full length of the elastic sheet in cross direction. The extension in cross direction may be varied depending on the elasticity of the material of the elastic sheet 13 and the number and lateral extension (in machine direction) of slits 14. For a given elastic material, the extension of the elastic sheet 13 in the cross direction and the number of slits are preferably chosen to provide an elongation of the closure tape 10 in the cross-direction prior to fastening it to the diaper, i.e. in the state shown in, for example, FIG. 2, of at least 5%, more preferably of at least 7% and especially preferably of at least 10% when applying a force of 15 N in cross-direction during the first elongation. The ratio of the extension of the elastic sheet 13 in the cross-direction over the length of closure tape 10 prior to fastening it to the diaper preferably is between 0.1 and 0.9, more preferably between 0.2 and 0.8 and especially preferably between 0.3 and 0.7. The extension of the elastic sheet 13 is cross direction preferably is between 10 and 40 mm and, more preferably between 10 and 25 mm.

The elastic sheet 13 may be made from a group of materials comprising essentially isotropic or essentially anisotropic materials. Useful elastic materials preferably exhibit an elongation at break as measured according to ASTM D 882 in the preferred direction of stretchability of at least 700% or more and, more preferably, of more than 850%.

Preferred essentially isotropically elastic materials include elastomeric polyurethane materials such as, for example, those available under the trademark ESTANE from B.F. Goodrich & Co., natural or synthetic rubber materials such as, for example, ethylene-propylene-dien copolymers (EPDM), styrene-butadiene-styrene block copolymers (SBS), styrene-(ethylene-butylene)-styrene block copolymers (SEBS) such as, for example, those available from the Shell Chemical Company under the trademark KRATON G like, for example, KRATON G-1657. Other elastomeric materials which may be used to form the elastic sheet 13 include elastomeric polyamide materials such as, for example, those available under the trademark PEBAX from the Rilsan Company and elastomeric polyester materials such as, for example, those available under the trade designation Hytrel from E.I. DuPont De Nemours & Company.

When attaching an essentially isotropic elastic material to the backing 11, the elasticity of the laminate in the machine direction will be essentially determined by the non-elastic and/or non-extensible, respectively, backing 11. Therefore essentially isotropically elastic materials can be used for the preparation of the closure tapes 10 of the present invention without rendering it unstable or wobbly in the machine direction.

Preferred essentially anisotropic elastic materials include extruded blends of a block copolymer elastomer portion and a polyolefin polymer portion, respectively, blended in a ratio from 10:1 to 0.4:1, wherein the block copolymer elastomer portion is formed of A blocks and B blocks, the A blocks being predominantly formed of monoalkenyl arenes and the B blocks predominantly of conjugated dienes and wherein the polyolefin polymer portion is comprised predominantly of an inelastic fiber forming polyolefin polymer, copolymer or blend. Such materials are described in copending U.S. patent application Ser. No. 08/720,794 filed by the present applicant on Oct. 4, 1996 now U.S. Pat. No. 5,885,908. JP 51-86,611 discloses extrusion of a blend of an ABA block copolymer with polystyrene where the polymers are exemplified as blended at a ratio of from 50 to 99 percent block copolymer to 1 to 50 percent polystyrene. The resulting material exhibits anisotropic behavior. Other essentially anisotropically elastic materials which are useful in the present invention are described, for example, in U.S. Pat. No. 5,344,691, U.S. Pat. No. 5,501,679 and U.S. Pat. No. 5,354,597.

Anisotropically elastomeric materials which are useful in the present invention preferably exhibit a ratio of the F10 force required to stretch a sheet of the elastomeric material (dimensions 20×25 mm) by 10% into the machine direction over the F10 forces required in the cross direction, of at least 1.5, more preferably of at least 2.0 and especially preferably of at least 2.5.

The elastic sheet 13 can be attached to the backing 11 by the adhesive layer in area 12b, and one or more slits or incisions 14 are applied in the area 12b extending from the outside surface of the backing 11 through the adhesive layer in area 12b to the upper surface of the elastic sheet 13 contacting the adhesive layer.

Figure 10:
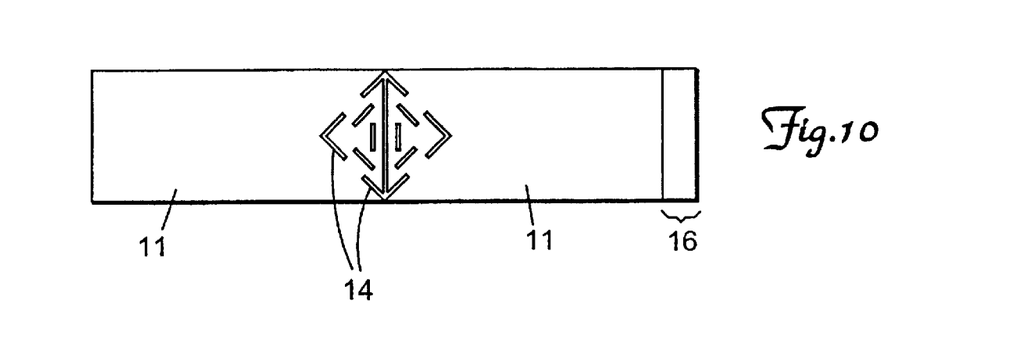
FIG. 10 is another embodiment of a closure tape 10 of the present invention (relaxed state) having in the area 12b of the elastic sheet 13 one full central incision and a number of partial incisions which are arranged to give the configuration of a parallelogram in the area 12b of the elastic sheet 13.

The extension of the incisions in the cross direction preferably is less than 10 $\mu$m, more preferably less than 50 $\mu$m and especially preferably between 10 and 30 $\mu$m. It was found that if the extension of the slits is less than approximately 25 $\mu$m, essentially no adhesive will be squeezed through the slits 14 on stretching and relaxing the closure tape 10 for several times, for example, for 3–5 times, so that the outer surface of the backing 11 remains essentially clean and is not contaminated with adhesive during use. The slits can be obtained by using a cutting wheel 52 as is shown in FIG. 10. The rotary cutting wheel 52 may comprise 1–8 circular knives separated from each other by typically 1.5–4 mm and results in slits with an approximate width of less than 100 $\mu$m and preferably not more than 50 $\mu$m. Rotary cutting wheels are commercially available from Dienes Werke, Overrath-Vilkerath, Germany. An example of a useful device is described in Example 1. It is also possible to apply the slits by using an approximately focused beam of a laser, such as, for example, of a $CO_2$ laser.

In the machine direction, the slits 14 may extend over the full width of the tape as is shown, for example, in FIG. 3, or over part of the width only as is shown, for example, in FIG. 10.

Figure 3A:
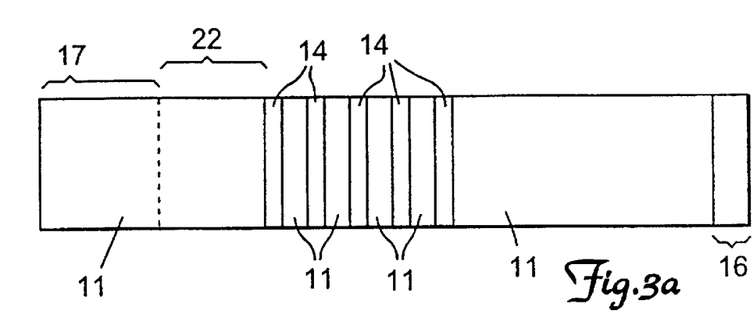
FIG. 3a is a top view of the closure tape 10 of FIG. 2 with a tension force being applied, showing that the incisions 14 have split apart to form essentially rectangular and essentially equally spaced openings.

When the slits extend over the full width of the closure tape 10 they will open on stretching without deforming or destroying the backing 11 exposing—depending on the construction of the closure tape—essentially rectangular strips of similar width of the adhesive layer of area 12b or the elastic sheet 13, respectively, as is shown in FIG. 3a. The elastic response of the closure tape 10 on stretching is essentially determined by the properties of the elastic sheet whereby the force required to obtain a desired elongation essentially depends on the properties of the elastic material, the number of slits extending over the entire width of the closure tape 10 in machine direction (also termed as full slits or incisions) and the density of slits per length unit.

Figure 9:
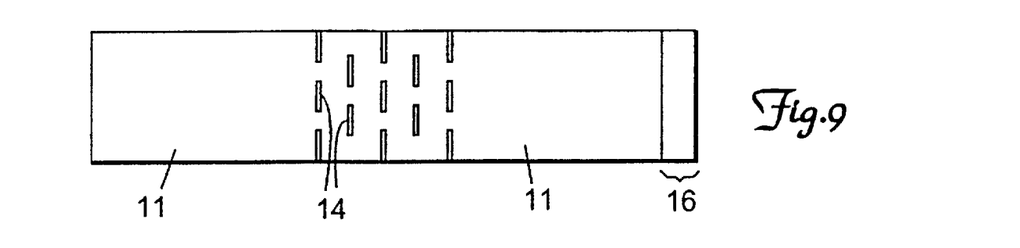
FIG. 9 is a top view of a closure tape in the relaxed state which is not an embodiment of the closure tape 10 of the present invention, said closure tape comprising a backing 11 having partial incisions 14 in the area of the elastic sheet 13, said partial slits being arranged in lines whereby the partial incisions of one line face the bridges between the partial incisions in an adjacent line.
Figure 9A:
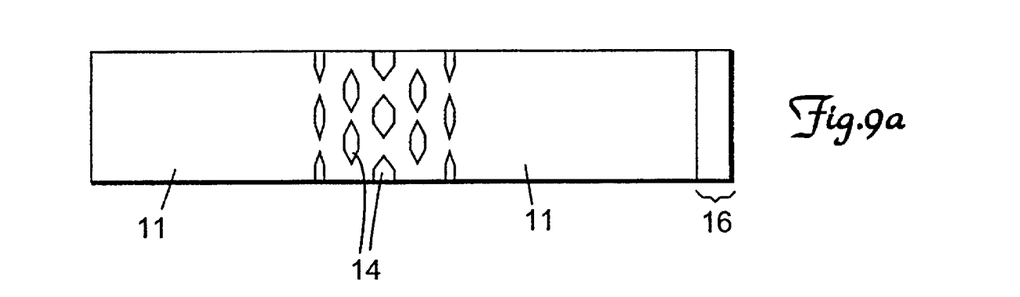
FIG. 9a is a top view of the closure tape of FIG. 9 with a tension force being applied, showing that the incisions have split apart to form essentially hexagonal openings, whereby the extension of the openings in cross direction is smaller for openings located in the outer lines.

In case the slits extend over part of the width of the closure tape 10 in machine direction (also termed as partial slits or incisions) as is shown, for example, in the configuration of FIG. 9, they will open on stretching to expose the elastic sheet 13 or the adhesive layer of area 12b, respectively, in openings of an essentially hexagonal shape as is shown in FIG. 9a. In case of such partial slits, the extension of the openings in the cross direction formed on stretching from slits located at different positions in the cross direction is less regular than in the case of full slits. The slits located in the outer lines of slits are being deformed to a lesser extent whereas the slits in the middle lines are stretched most. The response of the closure tape of FIG. 9 on stretching heavily depends on the properties of the non-elastic and/or non-extensible, respectively, backing 11 and is therefore essentially non-elastic. The bridges of the backing 11 between adjacent openings are irreversibly deformed for low elongations of the closure tape of, for example, approximately 5% or less, and the surface of the backing in the area 12b of the closure tape 10 remains rough and uneven on relaxation. Since the inelastic deformation of the backing 11 begins at very low elongations of the closure tape 10 already of, for example, approximately or less than 5%, the force required for initial stretching of the closure tape 10 is essentially determined by the stiffness or tenacity of the backing 11 and therefore usually distinctly higher than the force required for stretching a closure tape comprising at least one full slit by the same elongation.

The closure tapes 10 of the present invention therefore comprise one or more incisions 14 whereby at least one of the incisions extends in machine direction over the full width of the backing in the machine direction. The other slits present can be full or partial slits. Partial slits extending over at least 0.6 and, in particular, at least 0.75 of the full width of the closure tape 10 in machine direction are preferred. In a preferred embodiment of the closure tape 10 of the present invention at least 0.5 and, more preferably, at least 0.7 of the total number of slits are full slits. In an especially preferred embodiment of the closure tape 10 of the present invention, all slits are full slits.

The number of slits is preferably selected to give in combination with the elastic properties of the elastic sheet 13, the extension of the elastic sheet 13 in cross direction and the extension of the closure tape 10 in cross direction an elastic elongation of the closure tape 10 of the invention to a length of preferably at least 1.15, more preferably of at least 1.20 and especially preferably of at least 1.50 when stretching the closure tape in cross direction with a force of 15 N.

In case of full slits the number of slits preferably is at least 2, more preferably at least 3 and especially preferably at least 5. The density of slits preferably is between 1–10/cm and, more preferably, between 2–7/cm.

In case of partial slits being arranged in configurations like that in FIG. 10, the number of slits can vary over a wide range and preferably is at least 5, more preferably at least 10 with the density of partial slits being between 1–50/cm and, more preferably, between 1–30/cm.

Figure 11:
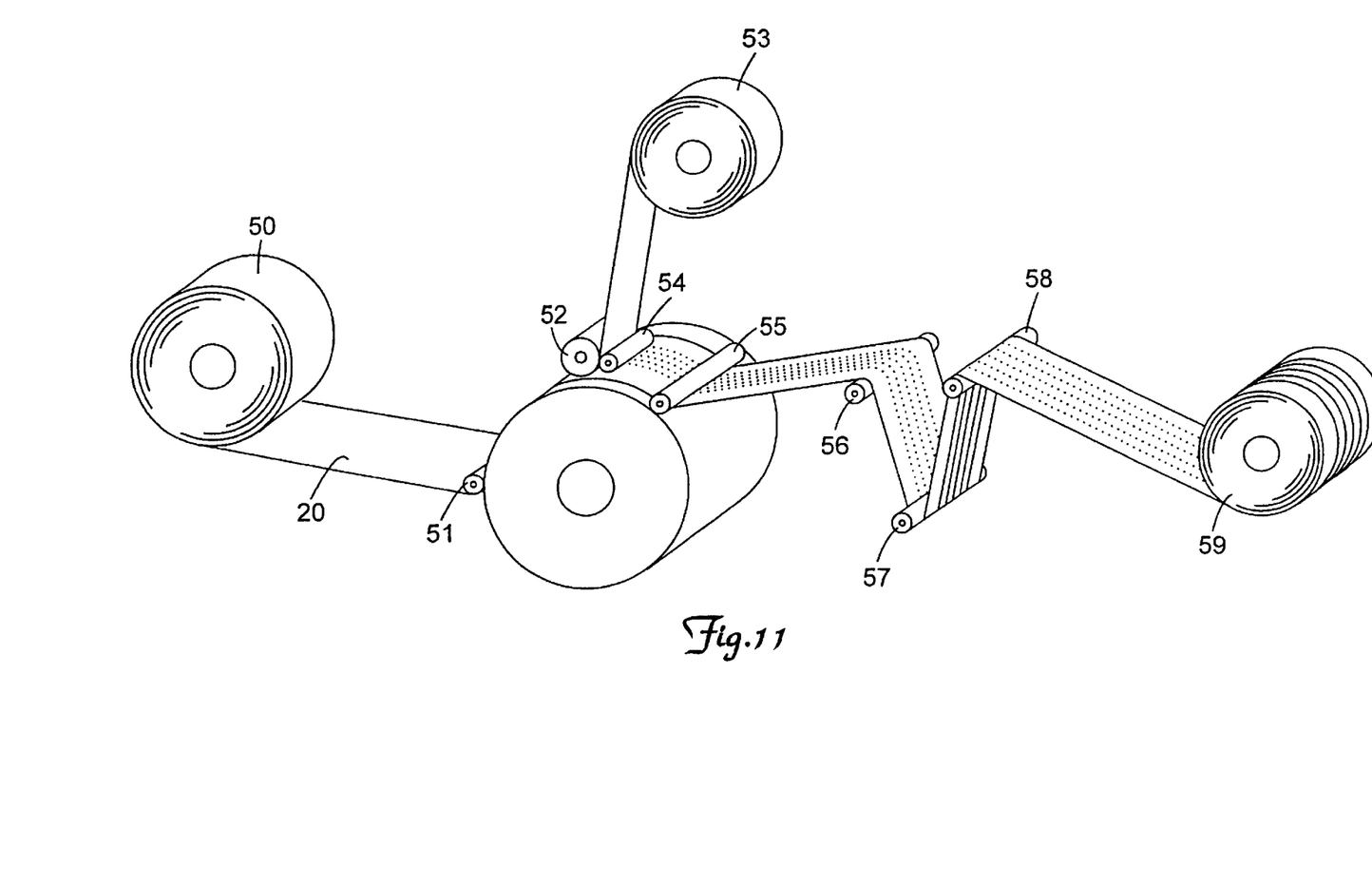
FIG. 11 is a schematic representation of a laminator for preparing laminates useful as precursors of closure tapes 10 of the present invention, said laminator comprising a supply roll 50 for the support sheet 20 comprising the backing 11 bearing the continuous or discontinuous adhesive layer 12, a rotary cutting wheel 52 for slitting the support sheet, a supply roll for the elastic sheet 13, a bonding roll 54 for bonding the elastic sheet to the support sheet, rollers 51, 55, 56, 57 and 58, and a storage roll 59 for the laminate.

The slits can be obtained after laminating the elastic sheet 13 to the backing 11 using the adhesive layer in area 12b, but the slits can also be obtained prior to laminating the elastic sheet 13 to the backing 11 in case appropriate measurements are taken to retain the physical integrity of the closure tape. FIG. 11 is a schematic representation of a laminator for preparing a laminate which is useful for preparing a closure tape 10 of the present invention. A backing 11 which is continuously or discontinuously covered with an adhesive layer 12 bearing, however, an adhesive layer at least in part of area 12b to anchor the elastic sheet 13 (see, for example, FIG. 2 and 8), is unwound from supply roll 50 and continuously slitted by rotary cutting wheel 52. An elastic sheet material is unwound from supply roll 33, and laminated to the slitted backing 11 by bonding roll 54 using the adhesive layer in area 12b. The backing 11 is fed to the rotary cutting wheel 52 via roller 51 and kept under tension by bonding roll 54 and roller 55 which is required to hold the strips obtained at the rotary cutting wheel 52 in place. The laminate obtained can then be wound onto storage roll 59.

The laminate prepared in the process of FIG. 11 comprising a backing 11, an adhesive layer at least in area 12b, an elastic layer 13 and slits 14 in area 12b can be processed further to attach a fastening means 15 and, optionally, further features such as, for example, a finger-lift 16, and can then be wound on a storage roll as a prelaminated closure tape in a stable roll from which the closure tape can be obtained by cutting in cross direction.

The fastening means 15 may comprise mechanical fastening means having engaging elements engagable with their contemplary counterpart on the target area 5. A suitable closure system comprises two interlocking means, one of them being a hook (or male) fastener means and the other being a loop (or female) fastener means. The fastening means 15 may comprise the hook fastener or the loop fastener means, respectively, but preferably comprises the hook fastener means. The hook fastener means may have any shape such as hooks, "T's" or any other shape as are well known in the art. The hook fastener material may be manufactured from a wide range of materials including nylon, polyester, polyolefins or any combination of these. A preferred hook material comprises a base and a plurality of engaging elements which comprise a stem supported at the base and an enlarged head which is positioned at the end of the stem opposite of the base. Such material is commercially available as Microreplicated Hook Material of a Mechanical Hook and Loop System, trade designation KN-2396 from 3M Company, St. Paul, U.S.A.

The loop material may be comprised of woven or non-woven fabric or any other suitable material which interlocks with the contemplary hook fastener material. A suitable loop fastening material comprises a number of fiber loops projecting from a woven backing such as the Knitted Loop Tape EKLT-1112, commercially available from 3M Company, St. Paul, U.S.A.

Alternatively, the adhesive layer in area 12d may be used as fastening means as was described above.

In a further alternative embodiment, another exposed adhesive layer which may optionally be applied to a carrier sheet, and which is attached to the backing 11 by the adhesive layer of area 12d, can be used as fastening means 15. The exposed adhesive layer is selected to give in combination with the target area 5 the desired adhesion and removability characteristic. The carrier sheet, if present, is selected to permanently bond the exposed adhesive layer to the adhesive layer in area 12d and may be selected, for example, from a group of materials comprising polyesters, polyethylenes, polypropylenes, polystyrenes, polycoated papers, polycarbonates or polymethylmethacrylates. The thickness of the carrier preferably is between 20 and 200 μm.

The fastening means 15 preferably has an extension in cross direction of between 10 and 40 mm, and more preferably of between 15 and 30 mm. The fastening means may extend over the full width of the closure tape in machine direction over the full length of its extension in cross direction but other configurations are also possible.

The finger-lift 16 may optionally be attached to the user's end to allow for easier handling of the closure tape 10. The finger-lift partly covers the adhesive layer in area 12e, if present, and has an extension in cross direction of typically between 3 and 10. Alternatively the finger-lift 16 may be attached to the backing 11 by different welding techniques such as, for example, ultrasonic welding. The finger-lift typically has a thickness of between 25 and 200 μm and is preferably prepared from a group of materials comprising polypropylene and polyesters.

DETAILED DESCRIPTION OF THE FIGURES

FIG. 1 shows a partially cutaway perspective representation of a disposable diaper in closed form which is described above.

The details of the closure tape 10 according to the invention are best shown in FIGS. 2–10.

FIG. 2 shows a preferred embodiment of a closure tape 10 according to the invention having a continuous adhesive layer 12 in areas 12a–12e which is attached to a backing 11. The same adhesive is preferably used in areas 12a–12e. The fastening means 15 preferably comprises a mechanical fastening means and, in particular, the hook (male) part of a mechanical closure system. The adhesive layer in area 12c provides an additional disposal feature which allows to secure the diaper filled with exudates after use when it is folded or rolled up in a configuration for disposal. The adhesive layer in area 12c may be covered with a release liner which is removed prior to use but it is also possible for the adhesive layer in area 12c to be exposed throughout use. The finger-lift 16 may extend over the whole area 12e to adjoin to the fastening means 15 but part of the adhesive layer in area 12e may be exposed, and optionally be covered with release liner.

Figure 4:
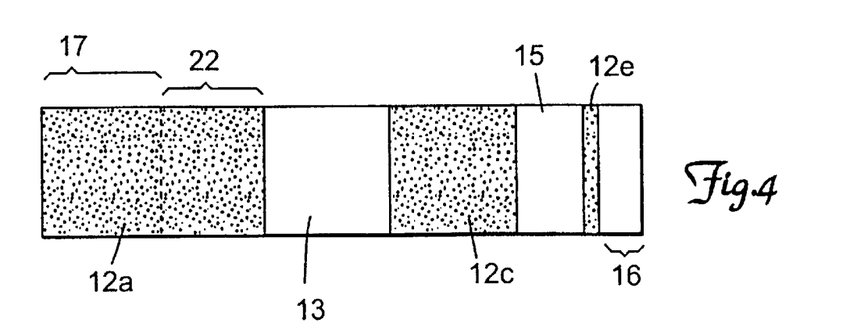
FIG. 4 is a bottom view of the embodiment of the closure tape 10 of FIG. 2 in the relaxed state showing the exposed continuous adhesive layer 12 in areas 12a, 12c and 12e, the end portion 17 of the closure tape to be attached to the outside surface 3 of the disposable diaper, the elastic sheet 13, the fastening means 15 and the finger-lift 16.

The fastening surface of the closure tape 10 of FIG. 2 which is reliably and yet removably adhered to the target area 5, is shown in the bottom view of FIG. 4 whereas the top view of FIG. 3 shows the non-bonding top side of the closure tape of FIG. 2, in the relaxed state (no tensile force applied). When stretching the closure tape of FIG. 2 in cross direction, the slits split apart forming essentially rectangular opening as is shown in the top view of FIG. 3a. The openings exhibit an essentially equal extension in cross direction and are essentially equally spaced from each other.

FIG. 5 shows the closure tape of FIG. 2 being attached to the outside surface 3 of a diaper 1 (peel mode type of attachment). The closure tape is preferably additionally secured by adhering release sheeting 19 carrying adhesive layer 18 onto the inside surface 2 of the diaper as is shown in FIG. 6 (shear mode type of attachment). The adhesive of adhesive layer 18 is preferably selected to permanently bond to the inside surface 2 of diaper 1. The release sheet 19 is preferably selected to allow for removable adhesion of the adhesive layer of area 12c and/or of the fastening means 15, respectively. Prior to use the closure tape 10 is folded onto the inside surface 2 of the diaper, and adhering the closure tape 10 to the inside surface 2 of the diaper is preferred in order to prevent the closure tape from "pop-open".

FIG. 7 gives a cross-sectional view of the closure tape of FIG. 2 being bent around the edge portion 6 of the diaper 1 to contact the inside surface 2 of the diaper. The diaper is usually stored prior to use and sold in the configuration of FIG. 7.

A cross-sectional view of an especially preferred embodiment of the closure tape 10 of the invention is shown in FIG. 8. The elastic sheet 13 is adhered to the backing 11 by small adhesive areas extending from area 12a and 12c, respectively, into area 12b whereas area 12b is essentially free of adhesive. The elastic sheet 13 may be additionally secured to the backing 11 by ultrasonic welding or other welding techniques. In the embodiment of FIG. 8 only one full slit may be used because no adhesive layer is present in area 12b and the part of the backing between the full slits would break off. Alternatively, it would be possible to use one full slit and several partial slits. Using no adhesive in area 12b of the closure tape 10 of FIG. 8 may be advantageous in order to avoid any leaking of adhesive through the slits onto the exposed surface of the backing 11.

FIG. 9 is a top view of a closure tape having lines comprising partial slits in the area of the elastic sheet 13 in the relaxed state (no tension force applied). In a line, partial slits and bridges between the slits are alternating and the slits of a line face bridges of the adjacent lines. The closure tape of FIG. 9 does not comprise at least one full slit and is therefore not an embodiment of the closure tape 10 according to the present invention. Upon stretching, the slits of the closure tape of FIG. 9 split apart to form essentially hexagonal openings. The extension of the openings in cross direction is distinctly smaller for slits being located in the outer lines as compared to slits in the middle lines (see FIG. 9a).

FIG. 10 is a top view of another closure tape 10 according to the invention having one central full slit and a number of partial slits which are arranged to give the configuration of a parallelogram.

FIG. 11 shows a schematic representation of a laminator for preparing a laminate useful for preparing a closure tape 10 according to the present invention. The backing comprising a continuous or discontinuous adhesive layer 12 and at least an adhesive layer in area 12b is unwound from supply roll 50 and fed via roller 51 into the rotary cutting wheel 52. If necessary, the supply roll 50 comprising the backing 11 bearing adhesive layer 12, may additionally comprise a release liner between the adhesive layer and the previous layer of the backing to facilitate unwinding. Such release liner if present is wound on a storage roll which is not shown in FIG. 10. The elastic sheet 13 is unwound from supply roll 53 and continuously laminated to the slitted backing 11 via bonding roll 54.

Figure 12:
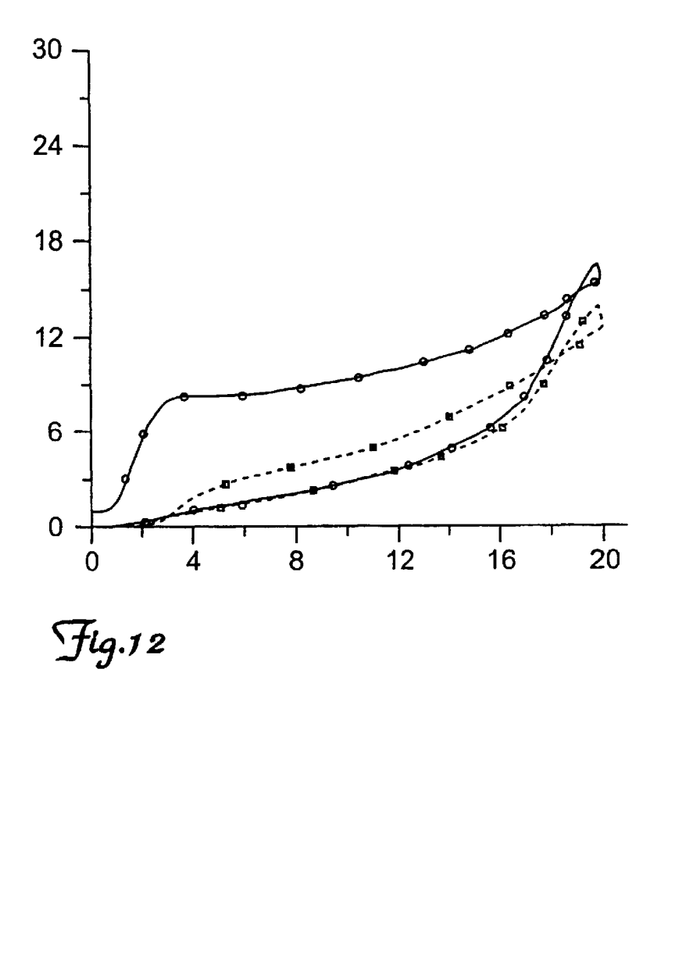
FIG. 12 is a hysteresis loss curve recorded for a laminate as shown in FIG. 9 having a backing 11 bearing a continuous adhesive layer 12, an elastic sheet 13 in area 12b and five parallel, equally spaced full incisions in the area 12b.
Figure 13:
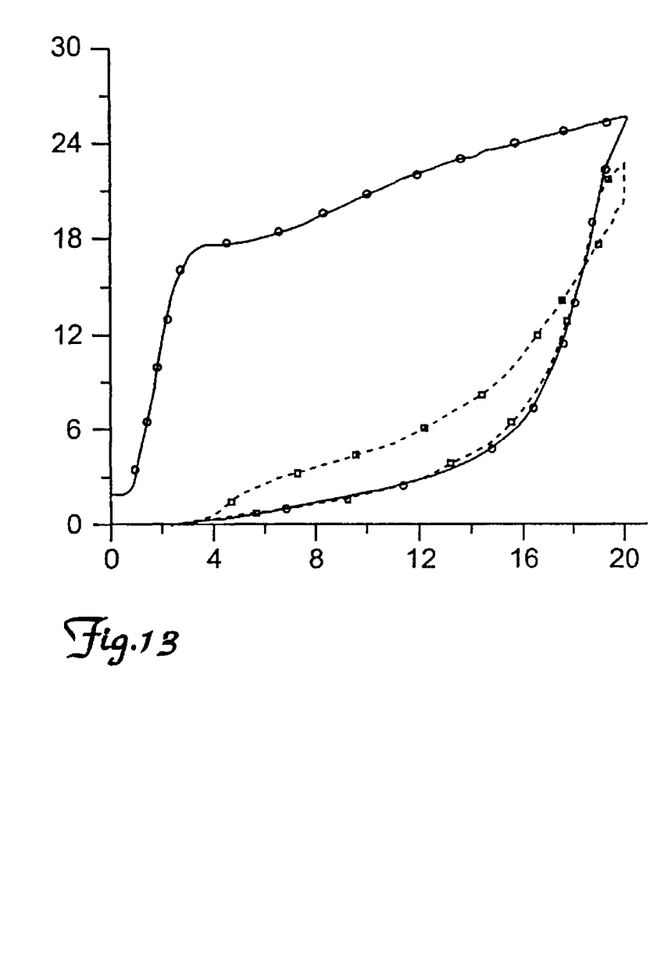
FIG. 13 is a hysteresis loss curve recorded for a laminate as shown in FIG. 10 having a backing 11 bearing a continuous adhesive layer 12, an elastic sheet 13 in area 12b and partial incisions arranged in five parallel and equally spaced lines in the area 12b.

FIGS. 12 and 13 are hysteresis loss curves recorded for 2 laminates prepared by using the laminator of FIG. 10. The hysteresis loss curve of FIG. 11 was recorded for a laminate comprising five full parallel incisions arranged in a configuration similar to that of FIG. 3. This is useful for preparing a closure tape 10 according to the invention. The hysteresis loss curve of FIG. 12 was recorded for a laminate comprising five parallel lines of partial slits arranged in a configuration similar to that of FIG. 9. The closure tape 10 which is obtainable from this laminate is not an embodiment of the present invention.

The invention will be further explained by the below examples. Numerical values of extensions, widths or lengths given above and below, refer to the relaxed state of the respective material, laminate or closure tape if not indicated otherwise. Before describing the examples a test method is described which is used to characterize the laminate and closure tape 10 of the present invention.

Test Method
Hysteresis Loss Measurement

A laminate which was prepared using the laminator of FIG. 10 and which had an extension in cross direction of 50 mm and in machine direction of 25 mm, was stretched in cross direction using a standard tensile test configuration as described in ASTM D 882 to an elongation of 130% with the extension in cross direction in the virgin state being defined as 100%. The laminate was then relaxed and a second stretching/relaxing cycle was subsequently run. The tensile tester speed was 254 mm/min and the initial tensile force was 0.2 N. The tensile force was measured as a function of the elongation during the virgin and the second test cycle.

EXAMPLES

Example 1

A laminate was obtained using the laminator of FIG. 11. A synthetic rubber elastic film 13 (sheath/core bicomponent fibers; core: 60% Vector 4211 from Exxon, 40% propylene 7060S from Fina; sheath: 100% propylene 7060S from Fina; sheath/core ratio=1:12, thickness 100 μm, 25 mm wide) was unwound from supply roll 53 and laminated to a pressure-sensitive adhesive tape comprising a propylene backing with a thickness of 110 μm bearing a SIS based pressure-sensitive adhesive which was unwound from storage roll 50 (roll width 50 mm). The adhesive tape is commercially available as Diaper Fastening Tape KE-700 from 3M Company, St. Paul, U.S.A. Prior to lamination in bonding roll 54 the pressure-sensitive adhesive tape was slit in rotary cutting wheel 52. The rotary cutting wheel was manufactured by Dienes Werke, Overrath-Vilkerath, Germany and comprised 5 circular knives of the type Controlleur (D1=76,96 mm, D2=19 mm, thickness 2 mm, material 1.2067). The resulting laminate exhibited 5 full parallel slits in the area 12b of the elastic sheet 13, the slits having an extension in cross direction of approximately 25 μm and being regularly spaced from each other by 2 mm. The configuration of slits correspond to that shown in FIGS. 3 and 3a. The laminate was obtained by unwinding it from storage roll 59 and cutting it in cross direction, thus obtaining laminates 50 mm in cross direction and 25 mm in machine direction.

The laminate was subjected to a hysteresis loss measurement described above, using the test parameters specified above. The hysteresis loss curve recorded is shown in FIG. 12.

Comparative Example 1

A laminate was prepared using the method of Example 1 using partial slits being arranged in 5 equally spaced lines. The configuration of slits corresponds to that shown in FIGS. 9 and 9a. The lines were regularly spaced from each other by 2 mm, and each line had 2 or 3 partial slits with a length of approximately 5 mm. The extension of the slits in cross direction was approximately 25 μm prior to stretching.

The closure tape was subjected to a hysteresis loss measurement described above using the test parameters specified above. The hysteresis loss curve recorded is shown in FIG. 3.

LIST OF REFERENCES

1—disposable diaper
2—inside surface
3—outside surface
4—absorbent core
5—target area
6—edge portion
10—closure tape
11—backing
12—adhesive layer
13—elastic sheet
14—incisions (also termed as slits)
15—fastening means
16—finger-lift
17—end portion of the closure tape to be attached to the outside surface 3 of the disposable diaper 1 (manufacturer's end)
18—adhesive layer
19—release sheeting
20—support sheet
21—user's end
22—distance between the manufacturer's end 17 and the incisision 14 closest to the manufacturer's end
50—supply roll for the backing bearing the adhesive layer
51, 55–58—roller
52—rotary cutting wheel
53—supply roll for elastic sheet
54—bonding roll
59—storage roll for laminate

What is claimed is:

1. Closure tape (10) for an absorbent article, particularly for a disposable diaper (1), for fastening of the article on the body of a person, the closure tape being attachable to the outside surface (3) of the diaper (1) through one of its end portions (17) and comprising a backing (11) having a first side and a second side, where the first side is provided with a continuous or discontinuous adhesive layer (12), a fastening means (15) and a stretchable elastic sheet (13) attached to the adhesive layer, the backing (11) being essentially non-elastic and/or essentially non-extensible, the support sheet (20) comprising the backing (11) and the continuous or discontinuous adhesive layer (12) exhibiting one or more incisions (14) in the area of the elastic sheet with at least one of the incisions extending in machine direction over the full width of the backing (11) and the end portion (17) being separated from the incision (14) closest to the end portion (17), by a sufficiently large distance (22) to prevent the incisions (14) essentially from opening when attaching the end portion (17) to the outside surface (3) of the diaper (1) and bending the remaining part of the closure tape (10) to contact the inside surface (2) of the diaper (1).

2. Closure tape according to claim 1 wherein the elastic sheet (13) is selected from a group of materials consisting of elastomeric polyurethanes, natural or synthetic rubbers, elastomeric polyamides or elastomeric polyesters and elastomeric polyolefins.

3. Closure tape according to claim 1 wherein the fastening means (15) comprises a mechanical fastening means and or pressure-sensitive adhesive layer.

4. Closure tape according to claim 1 wherein the backing (11) is selected from a group consisting of kraft paper, cellophane film, polymeric films, non-wovens, foamed materials and laminates.

5. Closure tape according to claim 1 wherein the incisions (14) have an average width in cross direction in the relaxed state of less than 100 $\mu$m.

6. Closure tape according to claim 1 wherein the number and extension of the incisions (14) in MD (length) is chosen as to allow for an elongation of a least 15% when applying a force of 20 N in CD.

7. Closure tape according to claim 1 wherein the distance (22) between the end portion (17) and the incision (14) closest to the end portion 17, is at least 2 mm.

8. Closure tape according to claim 1 additionally comprising a release sheeting (19) bearing an adhesive layer (18) to allow for securing the closure tape to the diaper (1) in a shear mode type of attachment.

9. Prelaminated closure tape in a stable roll from which the closure tape for an absorbent article according to claim 1 can be cut.

10. Absorbent article comprising a closure tape according to claim 1.

* * * * *